US00PP31066P3

(12) United States Plant Patent
Koot

(10) Patent No.: US PP31,066 P3
(45) Date of Patent: Nov. 12, 2019

(54) ***PORTULACA* PLANT NAMED 'DOPORCUPRASP'**

(50) Latin Name: *Portulaca oleracea*
Varietal Denomination: Doporcuprasp

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/732,823

(22) Filed: Jan. 3, 2018

(65) Prior Publication Data

US 2019/0208691 P1 Jul. 4, 2019

(51) Int. Cl.

| | |
|---|---|
| ***A01H 5/02*** | (2018.01) |
| ***A01H 6/00*** | (2018.01) |
| ***A01H 6/30*** | (2018.01) |

(52) U.S. Cl.
USPC ..... Plt./471
CPC ..... *A01H 6/00* (2018.05); *A01H 5/02* (2013.01); *A01H 6/30* (2018.05)

(58) Field of Classification Search
USPC ..... Plt./471
See application file for complete search history.

(56) References Cited

PUBLICATIONS

UPOV hit on *Portulaca* plant named 'Doporcuprasp', QZ PBR 20173402, filed Dec. 27, 2017.*

* cited by examiner

*Primary Examiner* — Anne Marie Grunberg
(74) *Attorney, Agent, or Firm* — C. A. Whealy

(57) ABSTRACT

A new and distinct cultivar of *Portulaca* plant named 'Doporcuprasp', characterized by its upright to low spreading growth habit; vigorous growth habit; freely branching habit; freely flowering habit; and large dark red purple-colored flowers.

1 Drawing Sheet

Botanical designation: *Portulaca oleracea.*
Cultivar denomination: 'DOPORCUPRASP'.

BACKGROUND OF THE INVENTION

The present invention relates to a new and distinct cultivar of *Portulaca* plant, botanically known as *Portulaca oleracea* and hereinafter referred to by the name 'Doporcuprasp'.

The new *Portulaca* plant is a product of a planned breeding program conducted by the Inventor in Rheinberg, Germany. The objective of the breeding program is to create new upright to spreading *Portulaca* plants with numerous large attractive flowers.

The new *Portulaca* plant originated from a cross-pollination made by the Inventor in Rheinberg, Germany in July, 2015 of a proprietary selection of *Portulaca oleracea* identified as code number RR-0058, not patented, as the female, or seed, parent with a proprietary selection of *Portulaca oleracea* identified as code number RR-0065, not patented, as the male, or pollen, parent. The new *Portulaca* plant was discovered and selected by the Inventor as a flowering plant from within the progeny of the stated cross-pollination in a controlled greenhouse environment in Rheinberg, Germany in May, 2017.

Asexual reproduction of the new *Portulaca* plant by vegetative terminal cuttings in a controlled greenhouse environment in Rheinberg, Germany since June, 2017, has shown that the unique features of this new *Portulaca* plant are stable and reproduced true to type in successive generations.

SUMMARY OF THE INVENTION

Plants of the new *Portulaca* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Doporcuprasp'. These characteristics in combination distinguish 'Doporcuprasp' as a new and distinct *Portulaca* plant:

1. Upright to low spreading growth habit.
2. Vigorous growth habit.
3. Freely branching habit.
4. Freely flowering habit.
5. Large dark red purple-colored flowers.
6. Good garden performance.

Plants of the new *Portulaca* can be compared to plants of the female parent selection. Plants of the new *Portulaca* differ primarily from plants of the female parent selection in the following characteristics:

1. Plants of the new *Portulaca* are more upright than and not as trailing as plants of the female parent selection.
2. Plants of the new *Portulaca* have larger flowers than plants of the female parent selection.
3. Plants of the new *Portulaca* and the female parent selection differ in flower color as plants of the female parent selection have dark pink-colored flowers.

Plants of the new *Portulaca* can be compared to plants of the male parent selection. Plants of the new *Portulaca* differ primarily from plants of the male parent selection in the following characteristics:

1. Plants of the new *Portulaca* are more upright than and not as trailing as plants of the male parent selection.
2. Plants of the new *Portulaca* have larger flowers than plants of the male parent selection.
3. Plants of the new *Portulaca* and the male parent selection differ in flower color as plants of the male parent selection have pink-colored flowers.

Plants of the new *Portulaca* can also be compared to plants of the *Portulaca hybrida* 'Duecupcheba', disclosed in U.S. Plant Pat. No. 25,809. In side-by-side comparisons, plants of the new *Portulaca* differ primarily from plants of 'Duecupcheba' in the following characteristics:

1. Plants of the new *Portulaca* are more upright than and not as trailing as plants of 'Duecupcheba'.
2. Plants of the new *Portulaca* have larger flowers than plants of 'Duecupcheba'.
3. Plants of the new *Portulaca* and 'Duecupcheba' differ in flower color as plants of 'Duecupcheba' have bright pink and yellow-colored flowers.

BRIEF DESCRIPTION OF THE PHOTOGRAPH

The accompanying colored photograph illustrates the overall appearance of the new *Portulaca* plant showing the colors as true as it is reasonably possible to obtain in colored reproductions of this type. Colors in the photograph may differ slightly from the color values cited in the detailed botanical description which accurately describe the colors of the new *Portulaca* plant. The photograph comprises a side perspective view of a typical flowering plant of 'Doporcuprasp' grown in a container.

DETAILED BOTANICAL DESCRIPTION

The aforementioned photograph and following observations, measurements and values describe plants grown during the spring and summer in 22-cm containers in a glass-covered greenhouse in Rheinberg, Germany and under cultural practices typical of commercial *Portulaca* production. During the production of the plants, day and night temperatures averaged 18° C. and light levels averaged 4,500 lux. Plants were pinched one time three weeks after planting and were 20 weeks old when the photograph and the description were taken. In the description, color references are made to The Royal Horticultural Society Colour Chart, 2007 Edition, except where general terms of ordinary dictionary significance are used.

Botanical classification: *Portulaca oleracea* 'Doporcuprasp'.

Parentage:

*Female, or seed, parent*.—Proprietary selection of *Portulaca oleracea* identified as code number RR-0058, not patented.

*Male or pollen parent*.—Proprietary selection of *Portulaca oleracea* identified as code number RR-0065, not patented.

Propagation:

*Type*.—By cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; close to 159C in color.

*Rooting habit*.—Freely branching; dense.

Plant description:

*Plant and growth habit*.—Upright to low spreading plant habit; vigorous growth habit.

*Branching habit*.—Freely branching habit about 200 to 250 lateral branches potentially developing per plant; pinching enhances branching potential.

*Plant height, soil level to top of foliar plane*.—About 23.5 cm.

*Plant height, soil level to top of floral plane*.—About 25 cm.

*Plant diameter* (*area of spread*).—About 80 cm.

Lateral branch description:

*Length*.—About 21 cm.

*Diameter*.—About 3 mm.

*Internode length*.—About 3 cm.

*Strength*.—Moderately strong.

*Texture and luster*.—Smooth, glabrous; glossy.

*Color, developing*.—Close to 146C; at the internodes, close to N199A.

*Color, fully developed*.—Close to N200A and 178A; at the internodes, close to N199A.

Leaf description:

*Arrangement*.—Alternate, simple.

*Length*.—About 2.5 cm.

*Width*.—About 1.5 cm.

*Shape, developing leaves*.—Elliptic.

*Shape, fully expanded leaves*.—Obovate.

*Apex*.—Cuspidate.

*Base*.—Attenuate.

*Margin*.—Entire.

*Texture and luster upper and lower surfaces*.—Smooth, glabrous; fleshy, succulent; semi-glossy.

*Venation pattern*.—Pinnate.

*Color*.—Developing leaves, upper surface: Close to 137A. Developing leaves, lower surface: Close to 147C. Fully expanded leaves, upper surface: Close to N137C overlain with close to 79C; venation, close to 150C. Fully expanded leaves, lower surface: Close to 148B overlain with close to 59A; venation, close to 150C.

*Petioles*.—Length: About 1.2 mm. Diameter: About 1.8 mm. Strength: Moderately strong. Texture and luster, upper and lower surfaces: Smooth, glabrous; glossy. Color, upper and lower surfaces: Close to 144B.

Flower description:

*Flower arrangement*.—Single rotate flowers; freely flowering habit with about 130 to 150 flower buds and flowers per plant at one time; flowers face mostly upright to outwardly.

*Fragrance*.—None detected.

*Natural flowering season*.—Plants begin flowering about twelve weeks after planting; in the garden, plants flower continuously from spring until autumn in Northern Europe.

*Flower longevity*.—Flowers last about one day on the plant; flowers not persistent.

*Flower diameter*.—About 3.1 cm.

*Flower length* (*height*).—About 1.5 cm.

*Flower buds*.—Length: About 1.3 cm. Diameter: About 6 mm. Shape: Ovoid. Texture and luster: Smooth, glabrous; semi-glossy. Color: Close to 144C and 47B.

*Petals*.—Quantity per flower and arrangement: Five petals in a single whorl. Length: About 1.6 cm. Width: About 1.7 cm. Shape: Obovate. Apex: Emarginate. Base: Truncate. Margin: Entire. Texture and luster, upper and lower surfaces: Smooth, glabrous; matte. Color: When opening, upper surface: Close to 51A. When opening, lower surface: Close to 38A and 18C. Fully opened, upper surface: Close to 60B; color does not change with development. Fully opened, lower surface: Close to 52B and 56D; color does not change with development.

*Sepals*.—Quantity per flower: Typically two fused into a tubular calyx. Calyx length: About 8.5 mm. Calyx diameter: About 5 mm. Length: About 8.5 mm. Width: About 5 mm. Shape: Ovate. Apex: Acuminate. Margin: Entire. Texture and luster, upper and lower surfaces: Smooth, glabrous; matte. Color, developing and fully developed, upper and lower surfaces: Close to 144A.

*Peduncles*.—Length: About 3 cm. Diameter: About 2 mm. Angle: Mostly upright. Strength: Moderately strong. Texture and luster: Smooth, glabrous; semi-glossy. Color: Close to 146C.

*Reproductive organs*.—Androecium: Quantity of stamens per flower: About 40 to 60. Filament length: About 4 mm to 5 mm. Filament color: Close to 167A. Anther shape: Oval, bi-lobed. Anther length: About 0.5 mm. Anther color: Close to 23A. Amount of pollen: Abundant. Pollen color: Close to 23A. Gynoecium: Pistil length: About 1 cm. Style length: About 5 mm. Style color: Close to 170B. Stigma color: Close to 163A. Ovary color: Close to 144A. Fruits: Quantity produced per plant: About 700 to 1,800 per plant at the end of the flowering season. Length: About 5 mm. Diameter: About 5.2 mm. Texture: Smooth, glabrous. Color: Close to 146D. Seeds: Quantity per flower: About 12 to 40. Length: About 1 mm. Diameter: About 1 mm. Texture: Smooth, glabrous. Color: Close to 202B and 200B.

Garden performance: Plants of the new *Portulaca* have been observed to have good garden performance, to tolerate temperatures ranging from about 7° C. to about 35° C. and to be suitable for USDA Hardiness Zone 11.

Pathogen & pest resistance: Plants of the new *Portulaca* have not been shown to be resistant to pathogens and pests common to *Portulaca* plants to date.

It is claimed:

1. A new and distinct *Portulaca* plant named 'Doporcuprasp' as illustrated and described.

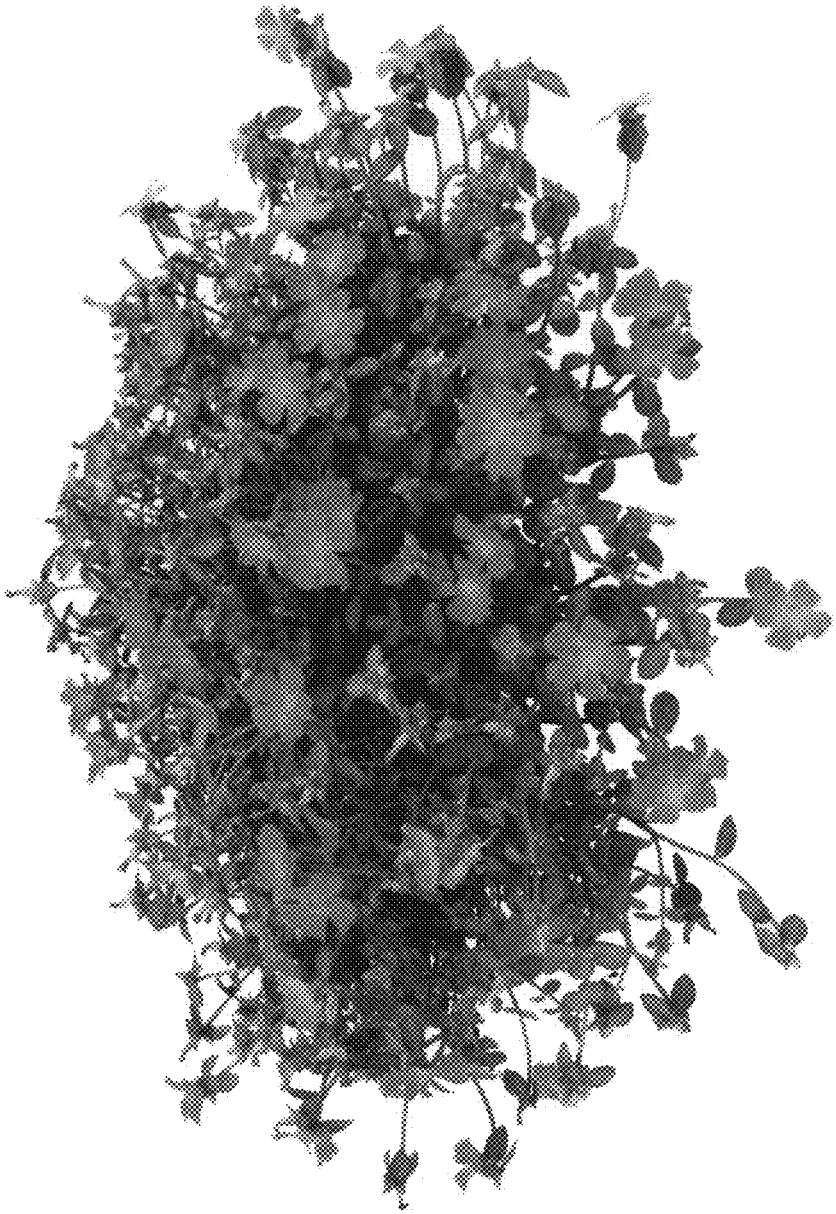

* * * * *